United States Patent [19]

Toda et al.

[11] Patent Number: 4,841,081
[45] Date of Patent: Jun. 20, 1989

[54] METHOD OF OPTICALLY RESOLVING A RACEMATE OR A DIASTEREOMERIC MIXTURE OF GLYCIDYL COMPOUND

[75] Inventors: Fumio Toda, Ehime; Koichi Tanaka, Matsuyama; Tetsuya Nakata, Ibaraki, all of Japan

[73] Assignee: Osaka Soda Co., Ltd., Osaka, Japan

[21] Appl. No.: 918,724

[22] Filed: Oct. 14, 1986

[30] Foreign Application Priority Data

Oct. 16, 1985 [JP] Japan .................. 60-230686
Nov. 8, 1985 [JP] Japan .................. 60-251597
Dec. 13, 1985 [JP] Japan .................. 60-281567

[51] Int. Cl.$^4$ ............. C07D 301/32; C07D 303/04; C07C 69/76; C07C 69/74
[52] U.S. Cl. ............................ 549/541; 549/546; 560/104; 560/109; 560/111; 560/118; 560/223; 560/248; 560/266
[58] Field of Search ........... 549/541, 546; 560/266, 560/111, 164, 223, 218, 109

[56] References Cited

PUBLICATIONS

F. Toda et al., Jour. Am Chem. Soc., vol. 105 (1983), pp. 5151-5152.
K. Tanaka et al., Chemical Abstracts, 100: 138870y.
K. Tanaka et al., J. Chem. Soc., Chem. Comm., vol. 24 (1983), pp. 1513-1514.
*Chemical Abstracts* (1985), 102, Abstract 203705f.
*Chemical Abstracts* (1988), 108, Abstract 167013s.

*Primary Examiner*—Richard L. Raymond
*Assistant Examiner*—Mark W. Russell
*Attorney, Agent, or Firm*—Sherman and Shalloway

[57] ABSTRACT

A method of optically resolving a racemate, or a diastereomeric mixture, of a substituted or unsubstituted glycidyl ester or ether compound having at least one glycidylic structure represented by the formula

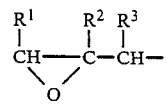

wherein $R^1$, $R^2$ and $R^3$, independently from each other, represent H or $CH_3$, and 1 to 3 asymmetric carbon atoms in the molecule, or a racemate of a beta-dihalohydrin ester compound, which comprises contacting said racemate or diastereomeric mixture with an optically active form of a compound having the following formula (I)

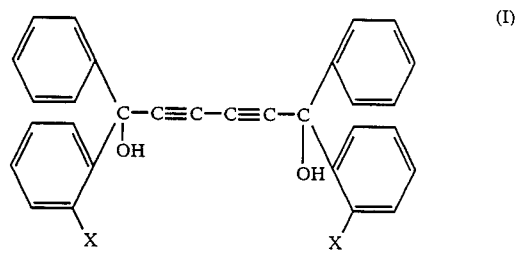

wherein X represents a halogen atom, to form an inclusion complex compound having the optically active compound of formula (I) as a host, and separating the resulting complex compound.

18 Claims, No Drawings

METHOD OF OPTICALLY RESOLVING A RACEMATE OR A DIASTEREOMERIC MIXTURE OF GLYCIDYL COMPOUND

This invention relates to a novel method of optically resolving a racemate, or a diastereomeric mixture, of a substituted or unsubstituted glycidyl ester or ether compound, or a racemate of a beta-dihalohydrin ester compound as a precursor of the glycidyl compound. More specifically, this invention relates to a novel method of optically resolving a racemate, or a diastereomeric mixture, or a glycidyl compound, which can give optically active compounds having a higher optical purity in a higher yield than known optical resolving methods for a racemate or a diasteromeric mixture of a glycidyl compound industrially advantageously and directly without changing the highly reactive epoxy group of the glycidyl compounds.

In particular, this invention relates to a method of optically resolving a racemate, or a diastereomeric mixture, of a substituted or unsubstituted glycidyl ester or ether compound having at least one glycidylic structure represented by the formula

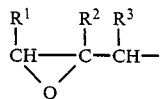

wherein $R^1$, $R^2$ and $R^3$, independently from each other, represent H or $CH_3$, and 1 to 3 asymmetric carbon atoms in the molecule, or a racemate of a beta-dihalohydrin ester compound, which comprises contacting said racemate or diastereomeric mixture with an optically active form of a compound having the following formula (I)

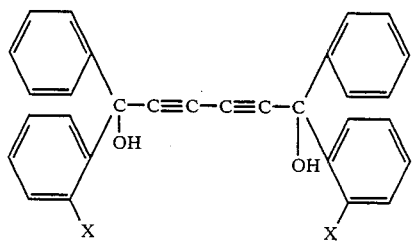

wherein X represents a halogen atom, to form an inclusion complex compound having the optically active compound of formula (I) as a host, and separating the resulting complex compound.

In the following description, the substituted or unsubstituted glycidyl compound may sometimes be generically referred to as a glycidyl compound. The optical resolution of the racemate and the optical resolution of the diasteromeric mixture may sometimes be referred to generically as the optical resolution of a racemate.

Glycidyl compounds are very industrially valuable as intermediates for synthesis of various derivatives and as polymerizable monomers for production of useful polymers or copolymers. It has recently been well known that in a chemical substance having a biological function, one of its optical isomers has a special significance. It is very significant to obtain optically active glycidyl compounds as materials for the synthesis of biologically functioning substances. Furthermore, in the polymer chemical industry, too, it is significant to synthesize polymers having only a specific steric configuration because it results in formation of polymers having a specific function.

In the prior art, the production of optically active glycidyl compounds requires the use of natural optically active substances as starting materials, or the preparation of optically active precursors by an operationally complex and disadvantageous microbiological method and the subsequent synthesis of optically active glycidyl compounds from the precursors. Alternatively, it is necessary to subject a glycidyl compound to a chemical reaction with an optically active compound to convert it into another compound, and then to subject the other compound to a chemical reaction to obtain the desired optically active glycidyl compound.

Thus, in the prior methods of obtaining optically active glycidyl compounds which are industrially disadvantageous, very inefficient operations are required, and moreover, the optical purities of the resulting optically active glycidyl compounds are low, or only one of the enantiomorphs can be obtained.

Some of the coinventors of the present application previously discovered that a cyclic ketone having an alkyl substituent, particularly a cyclic ketone of the following formula

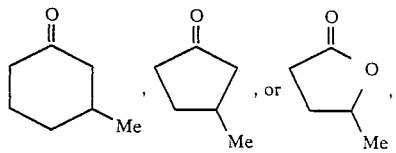

can be optically resolved by utilizing the compound of formula (I). They reported it in a paper entitled "Optical Resolution of 3-Methylcycloalkanones and 5-Methyl-gamma-butyrolactone by Complexation with Optically Active 1,6-bis(o-Halophenyl)-1,6-diphenylhexa-2,4-diyne-1,6-diol" (J. Am. Chem. Soc., 1983, 5151). Furthermore, some of the coinventors of the present invention reported that five bicyclic lactones and three bicyclic ketones can be optically resolved by utilizing the compound of formula (I) (Chemistry Letters, 1985, 885).

These prior references, however, neither describe nor suggest the optical resolution of a racemate of a glycidyl compound. Furthermore, the prior optical resolution of a compound having a glycidyl group requires a step of ring-opening the glycidyl ring because of the high reactivity of the glycidyl group.

The present inventors have made investigations in order to develop a method which can advantageously overcome the aforesaid technical troubles in the optical resolution of a racemate of a glycidyl ester or ether compound or a racemate of a beta-dihalohydrin ester compound which is a precursor of the glycidyl ester compound.

These investigations have led to the discovery that by contacting the racemate with the optically active form of the compound of formula (I), an inclusion complex compound containing only one of the enantiomorphs of the racemate as a guest and the optically active compound of formula (1) as a host can be easily formed and isolated; the guest compound as one enantiomorph can be easily separated and obtained from the complex compound; and the other enantiomorph can be easily obtained from the residue left after isolation of the inclusion complex compound.

It has also been found that the inclusion complex compound can be formed industrially advantageously with high selectively and in a high yield and purity without changing the glycidyl group.

It is an object of this invention to provide a much improved method of optically resolving a racemate, or a diastereomeric mixture, of a glycidyl ester or ether compound, or a racemate of a beta-dihalohydrin ester compound.

The above and other objects of this invention along with its advantages will become more apparent from the following description.

According to the method of this invention, a racemate, or a diastereomeric mixture, of a substituted or unsubstituted glycidyl ester or ether compound having at least one glycidylic structure represented by the following formula

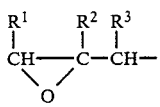

wherein $R^1$, $R^2$ and $R^3$, independently from each other, represent H or $CH_3$, and 1 to 3 asymmetric carbon atoms in the molecule, or a racemate of a beta-dihalohydrin ester compound is contacted with an optically active form of a compound having the following formula (I)

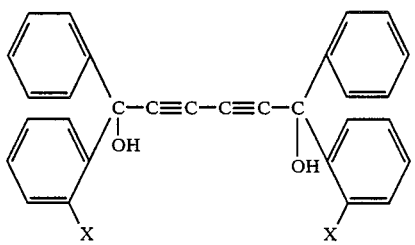

wherein X represents a halogen atom, to form an inclusion complex compound containing the compound of formula (I) as a host compound, and the resulting complex compound is separated from the reaction system. The reaction of forming the inclusion complex compound can be carried out with high selectivity using one of the enantiomorphs constituting the racemate as a guest compound. The other enantiomorph remains in the reaction system and can be recovered from it.

If the glycidyl compound to be resolved has at least 2 asymmetric carbon atoms in the molecule, this compound is present as a diastereomeric mixture. In the prior art, the isolation of optical isomers from a diastereomeric mixture should, in almost all cases, be carried out by first separating the mixture into the individual diastereomers by some method, and optically resolving the separated diastereomers.

According to the method of this invention using the optically active compound of formula (I) as a host, contacting of the diastereomeric mixture directly with the compound of formula (I) makes possible direct isolation of at least one optical isomer. When the compound of formula (I) forms complexes with two or more optical isomers, the rates of forming the complexes are different in many cases, and the complexes can be easily separated. Where there is no difference in the rate of forming at least two complexes under one set of conditions, such complexes may be easily separated by recrystallization using different solvents. By adding the other enantiomorph of the compound of formula (I) to the residue left after removal of the formed complexes, a complex containing the other enantiomorph of the glycidyl compound as a guest can be precipitated and isolated.

Examples of the racemate, or the diastereomeric mixture, of a substituted or unsubstituted glycidyl ester or ether compound having at least one glycidylic structure represented by the formula

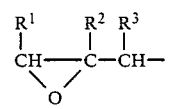

wherein $R^1$, $R^2$ and $R^3$, independently from each other, represents H or $CH_3$ and 1 to 3 asymmetric carbon atoms in the molecule as used in the present invention are racemates, or diastereomeric mixtures, of glycidyl ester compounds represented by the following formula (II)-1 and racemates, or diastereomeric mixtures, of glycidyl ether compounds represented by the following formula (II)-2. Examples of the racemate of a beta-dihalohydrin ether compound are racemates of compounds represented by the following formula (II)-3.

Substituted or unsubstituted glycidyl ester compounds represented by the formula (II)-1

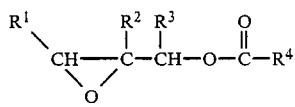

wherein $R^1$, $R^2$ and $R^3$, independently from each other, represent H or $CH_3$, and $R^4$ represents an alkyl group, preferably a $C_1$-$C_6$ alkyl group, especially preferably a $C_1$-$C_4$ alkyl group, an aryl group, preferably a $C_6$-$C_{10}$ aryl group such as a phenyl or naphthyl group, an arylalkyl group, preferably a $C_6$-$C_{10}$ aryl-$C_1$-$C_2$ alkyl group, an arylalkenyl group, preferably a $C_6$-$C_{10}$ aryl-$C_2$-$C_4$ alkenyl group, or an alkenyl group, preferably a $C_2$-$C_4$ alkenyl group, and when $R^4$ represents an alkyl group, $R^1$ and $R^3$ may together form the moiety

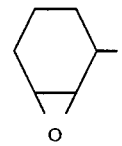

together with

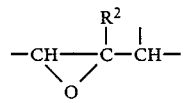

in the formula.

Substituted or unsubstituted glycidyl ether compounds represented by the formula (II)-2

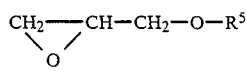 (II)-2 wherein $R^5$ represents an alkyl group, preferably a $C_1$-$C_6$ alkyl group, especially preferably a $C_1$-$C_4$ alkyl group, an aryl group, preferably a $C_6$-$C_{10}$ aryl group such as a phenyl or naphthyl group, an alkenyl group, preferably a $C_2$-$C_4$ alkenyl group, or the group

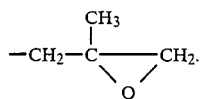

beta-Dihalohydrin ester compounds represented by the formula (II)-3

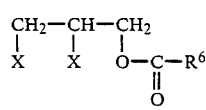 (II)-3 wherein X represents a halogen atom such as Cl, Br, I or F, $R^6$ represents an alkyl group, preferably a $C_1$-$C_6$ alkyl group, especially preferfably a $C_1$-$C_4$ alkyl group, an aryl group, preferably a $C_6$-$C_{10}$ aryl group such as a phenyl or naphthyl group, an arylalkyl group, preferably a $C_6$-$C_{10}$ aryl-$C_1$-$C_2$ alkyl group, an arylalkenyl group, preferably a $C_6$-$C_{10}$ aryl-$C_2$-$C_4$ alkenyl group, or an alkenyl group, preferably a $C_2$-$C_4$ alkenyl group.

Specific examples of the glycidyl ester compounds of formula (II)-1 are given below. In the following examples, the asterisks attached to carbon atoms show that they are asymmetric carbon atoms.

Glycidyl acetate

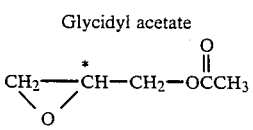

2-Methylglycidyl acetate

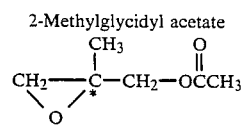

Glycidyl propionate

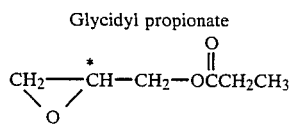

Glycidyl butyrate

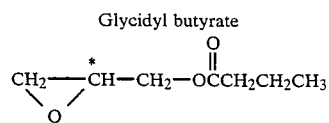

Glycidyl benzoate

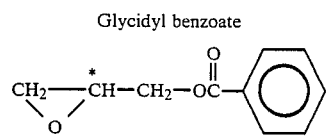

Glycidyl cinnamate

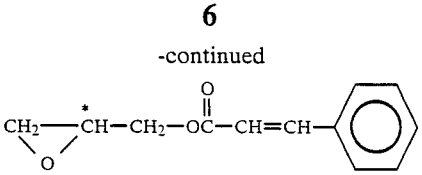

Glycidyl alpha-naphthoate

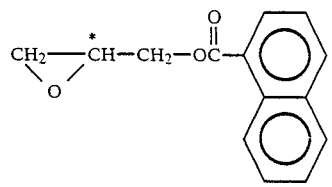

Glycidyl beta-naphthoate

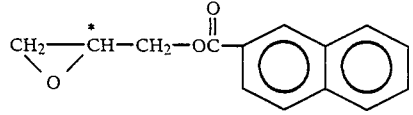

Glycidyl alpha-naphthylacetate

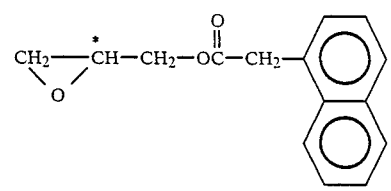

Glycidyl beta-naphthylacetate

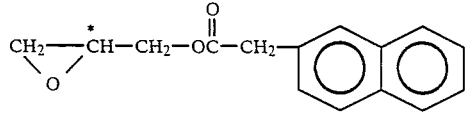

Glycidyl alpha-naphthoxyacetate

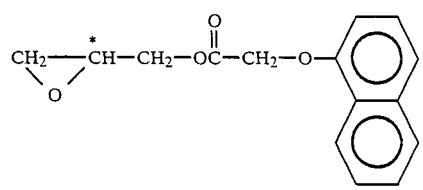

Glycidyl beta-naphthoxyacetate

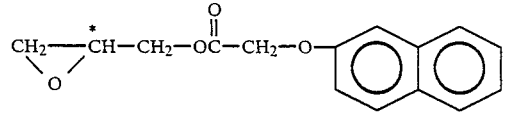

Glycidyl acrylate

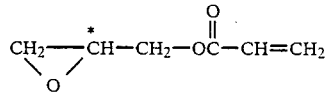

Glycidyl methacrylate

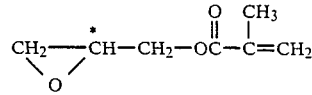

1-Methyl-2,3-epoxy-propyl acetate

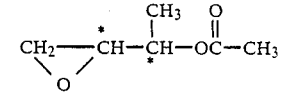

2,3-Epoxybutyl acetate

-continued

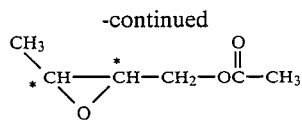

1-Methyl-2,3-epoxy-butyl acetate

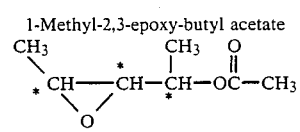

2,3-Epoxy-cyclohexyl acetate.

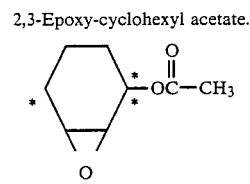

Specific examples of the glycidyl ether compounds of formula (II)-2 are given below Methyl glycidyl ether

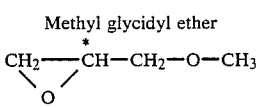

Allyl glycidyl ether

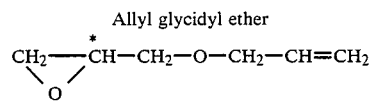

n-butyl glycidyl ether

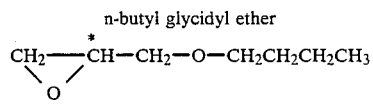

iso-Butyl glycidyl ether $$\text{CH}_2\overset{*}{\underset{O}{\diagdown\!\!/}}\text{CH}-\text{CH}_2-\text{O}-\text{CH}_2\text{CH}\overset{\text{CH}_3}{\underset{\text{CH}_3}{\diagup}}$$

Phenyl glycidyl ether

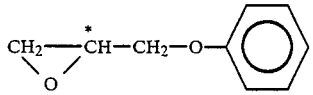

alpha-Naphthyl glycidyl ether

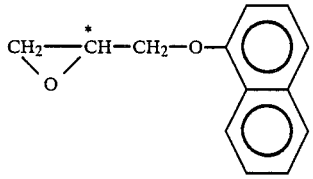

beta-Naphthyl glycidyl ether

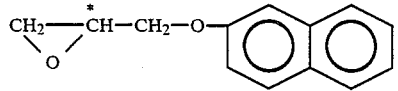

2,3-Epoxypropyl-2',3'-epoxy-2'-methylpropyl ether

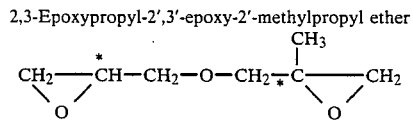

Diglydicyl ether (bis-2,3-epoxypropyl ether)

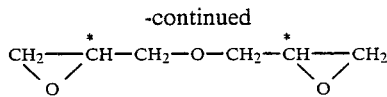

Specific examples of the beta-dihalohydrin ester compound of formula (II)-3 are given below.

1-Acetoxy-2,3-dichloropropane

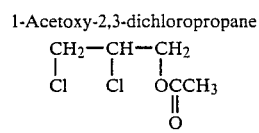

1-Butanoxy-2,3-dichloropropane

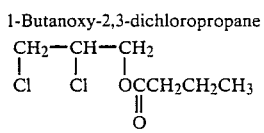

1-Acetoxy-2,3-dibromopropane

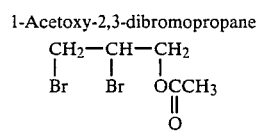

In the method of this invention, the racemate, or the diastereomeric mixture, of the glycidyl ester or ether compound defined above or the racemate of the beta-dihalohydrin ester compound defined above is contacted with an optically active form of a compound having the following formula (I).

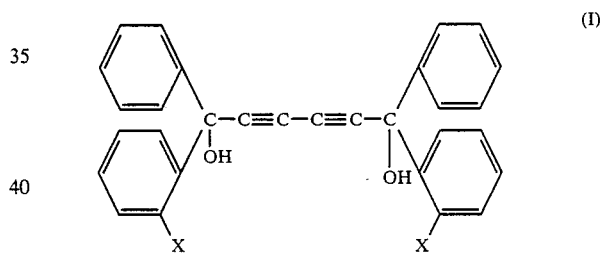

wherein X represents a halogen atom.

The compound of formula (I) is a known compound, and examples of the halogen atom X are Cl, Br, I and F. The optically active compound of formula (I) can be produced easily by oxidatively coupling a known optically active compound represented by the following formula

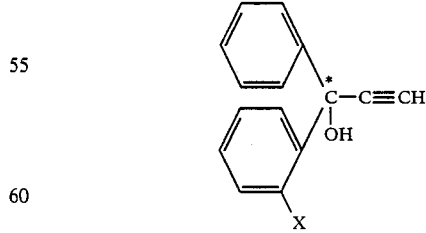

wherein X is as defined with regard to formula (I), for example by oxidizing it with air in acetone as a solvent in the presence of a cuprous chloride/pyridine catalyst. Examples of the compound of formula (I) so obtained include 1,6-di-o-chlorophenyl-1,6-diphenylhexa-2,4-diyne-1,6-diol, 1,6-di-o-bromophenyl-1,6-diphenylhexa- 2,4-diyne-1,6-diol and 1,6-di-o-fluorophenyl-1,6-diphenylhexa-2,4-diyne-1,6-diol.

According to the method of this invention, the racemate of the glycidyl ester or ether compound of the racemate of the beta-dihalohydrin ester compound is contacted with the optically active form of the compound of formula (I) to form easily and selectively an inclusion complex compound containing the optically active compound (I) as a host compound and one of the enantiomorphs of the racemate as a guest compound.

The reaction of forming the inclusion complex compound containing the optically active compound of formula (1) as a host by the above contacting treatment can be carried out by directly mixing the optically active compound of formula (I) and the racemate of the guest compound, or mixing them as solutions. Examples of the solvent which may be utilized in reacting the two reactants in the presence of solvent include aliphatic hydrocarbons such as pentane, hexane, cyclohexane, heptane, petroleum ether and petroleum benzine; aromatic hydrocarbons such as benzene and toluene; ethers such as diethyl ether, dipropyl ether, diisopropyl ether, dioxane and tetrahydrofuran; halogenated hydrocarbons such as dichloromethane and dichloroethane; and suitable mixtures of these.

The reaction conditions may be properly chosen and varied depending upon, for example, the mode of the contacting treatment, the type of the solvent and the types of the two reactants. For example, the reaction temperature is from room temperature to the refluxing temperature of the solvent. The reaction time can be varied properly depending upon the reaction temperature and the above-mentioned factors. Since the inclusion complex compound formed as a result of the reaction usually precipitates as solid crystals, the reaction time can be easily selected and determined by using the formation of the precipitate as a measure. Precipitation of the crystals may take place immediately after the contacting of the host compound with the guest compound, of sometimes after a lapse of about 1 hour to about several tens of hours.

The inclusion complex compound formed by the contacting treatment and containing the optically active compound of formula (I) as a host and one of the enantiomorphs of the racemate as a guest usually has a guest-/host mole ratio of from 3/1 to 1/3. Accordingly, in performing the reaction, the proportions of the guest compound and the host compound used are preferably selected so that about 0.25 to about 4 moles of the guest compound is used per mole of the host compound depending upon the types of these compounds.

By separating the inclusion complex compound from the reaction mixture, one of the enantiomorphs of the racemate can be obtained in the form of an inclusion complex compound. Since the resulting inclusion complex compound precipitates from the reaction system, it can be easily recovered by utilizing a solid-liquid separating means such as filtration, and as required it may be purified by, for example, recrystallization.

The optically active guest compound can be obtained from the separated inclusion complex compound containing the optically active glycidyl ester or ether compound or the optically active beta-dihalohydrin ester compound as a guest and the optically active compound as a host by a known means such as distillation under heat, substitution by a polar solvent, or chromatography. For example, according to the distillation method, the inclusion complex compound is distilled by heating it under reduced pressure to obtain the optically active guest compound as a distillate. In the method of substitution with a polar solvent, the optically active guest compound can be obtained by using a ketone such as acetone or methyl ethyl ketone or an ester such as ethyl acetate. In the chromatographic method, the optically active guest compound may be obtained by using a solvent such as dichloroethane.

The other enantiomorph of the racemate is present in the residue resulting from separation of the inclusion complex compound from the reaction system. Hence, the other optically active compound can be obtained by, for example, distillation, or by adding the other enantiomorph of the host compound and forming an inclusion complex containing the other enantiomorph of the racemate as a guest.

The following Examples illustrate the method of this invention more specifically.

EXAMPLE 1

Optically pure levorotatory 1,6-di-o-chlorophenyl-1,6-diphenyl-hexa-2,4-diyne-1,6-diol ($[\alpha]_D = 122°$; mp. 127°–129° C.; 9.66 g (0.02 mole)) and 5.76 g (0.04 mole) of racemic glycidyl butyrate were dissolved in a mixed solvent composed of 10 ml of ether and 20 ml of petroleum ether, and refluxed for 12 hours. The reaction mixture was filtered to collect 11.0 g of colorless prismatic crystals (yield 88%). The crystals were a complex in which the above compounds were included in a mole ratio of 1:1. The complex had a melting point of 72° to 75° C. and a specific rotation, measured with a methanol solution, $[\alpha]_D$ (the same solvent was used in measuring the specific rotation hereinafter), of $-93.5°$.

The crystals were when then thermally decomposed under reduced pressure to distill levorotatory glycidyl butyrate which had a $[\alpha]_D$ of $-5.7°$.

The above prismatic crystals were recrystallized five times to give crystals having a melting point of 72° to 75° C. and a $[\alpha]_D$ of $-94.1°$. These crystals were thermally decomposed under reduced pressure as above to give levorotatory glycidyl butyrate having a $[\alpha]_D$ of $-11.8°$.

The filtrate from which the prismatic crystals had been separarted was distilled to give 3.2 g of dextrorotatory glycidyl butyrate which had a $[\alpha]_D$ of $+4.26°$.

EXAMPLE 2

The same levorotatory 1,6-o-chlorophenyl-1,6-diphenyl-hexa-2,4-diyne-1,6-diol (4.83 g; 0.01 mole) and 3.0 g (0.02 mole) of racemic phenyl glycidyl ether were dissolved in a mixed solvent composed of 5 ml of ether and 20 ml of petroleum ether. The solution was refluxed for 12 hours. After cooling the reaction mixture, 4.65 g (yield 73%) a complex in which the mole ratio of the above compounds was 1:1 was obtained as colorless prismatic crystals. These crystals had a melting point of 79° to 80° C., and a $[\alpha]_D$ of $-90.6°$.

The crystals were then distilled under reduced pressure to give levorotatory phenyl glycidyl ether having a $[\alpha]_D$ of $-1.4°$.

The prismatic crystals were recrystallized once to give crystals having a melting point of 79° to 81° C. and a $[\alpha]_D$ of $-92.9°$. Distillation of these crystals under reduced pressure gave phenyl glycidyl ether having a $[\alpha]_D$ of $-2.7°$.

EXAMPLE 3

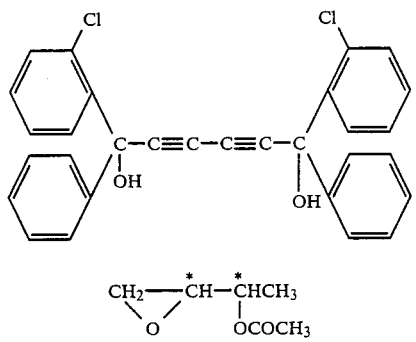

Optically pure levorotatory 1,6-di-o-chlorophenyl-1,6-diphenylhexa-2,4-diyne-1,6-diol ($[\alpha]_D = -122°$, mp. 127°–129° C.; 2.42 g) and 1.30 g of a diastereomeric mixture of 1-methyl-2,3-epoxypropyl acetate (threo:erythro=64:36) were dissolved in a mixed solvent (1:1) composed of ether and petroleum ether, and the solution was left to stand at room temperature for 12 hours. It was filtered, and the resulting complex in the form of crystals were recrystallized once from the above mixed solvent, filtered, and dried to give 0.76 g of colorless prismatic crystals. These crystals were a complex in which the mole ratio of (−)-A to threo-(+)-B was 1:1. The complex had a melting point of 101° to 103° C. and a $[\alpha]_D$ of −92.2°.

The crystals were heated to about 150° C. under reduced pressure (25 mmHg) to obtain 0.16 g of threo-(+)-B ($[\alpha]_D = +1.0°$).

EXAMPLE 4

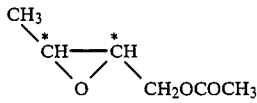

The same (−)-A as used in Example 3 (2.42 g) and 1.30 g of a diastereomeric mixture of 2,3-epoxybutyl acetate represented by formula (C) above were dissolved in 10 ml of the same mixed solvent as used in Example 3, and then left to stand at room temperature for 12 hours. It was filtered to give a complex as crystals. The crystals were recrystallized twice from the mixed solvent, filtered, and dried to give 0.95 g of colorless needle-like crystals. These crystals were a complex in which the mole ratio of (−)-A to (+)-C was 1:1. The complex had a melting point of 117° to 119° C. and a $[\alpha]_D$ of −82.0° C.

When the crystals were heated as in Example 3, 0.20 g of (+)-C ($[\alpha]_D = +50.6°$) was obtained.

Separately 2.42 g of the enantiomorph (+)-A of A was added to the mother liquor left after separating the above complex by filtration, and the mixture was left to stand at room temperature for 12 hours. The resulting crystals were recrystallized twice from the same mixed solvent as above to give 0.88 g of a complex having a $[\alpha]_D$ of +82.0°.

When the complex was heated in the same way as in Example 3, 0.155 g of (−)-C ($[\alpha]_D = -50.6°$) was obtained.

EXAMPLE 5

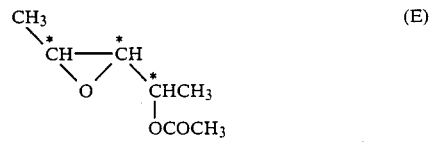

The same (−)-A as in Example 3 (4.83 g) and 2.88 g of a diastereomeric mixture of 1-methyl-2,3-epoxybutyl acetate (threo:erythro=9:91) were dissolved in 20 ml of the same mixed solvent as in Example 3, and left to stand at room temperature for 12 hours. The crystals of a complex obtained by filtration were recrystallized twice from the same mixed solvent as above, filtered, and dried to give 1.72 g of colorless prismatic crystals. These crystals were a complex in which the mole ratio of (−)-A to erythro-(−)-E was 1:1. The complex had a melting point of 105° to 108° C. and a $[\alpha]_D$ of −104°.

When these crystals were heated in the same way as in Example 3, 0.4 g of erythro-(−)-E ($[\alpha]_D = -13.0°$) was obtained.

EXAMPLE 6

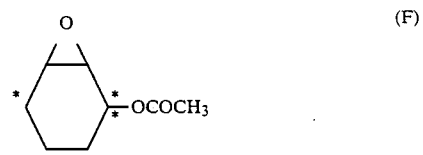

The same (−)-A as in Example 3 (4.83 g) and 3.12 g of a diastereomeric mixture of 2,3-epoxycyclohexyl acetate (cis:trans=35:65) were dissolved in 20 ml of the same mixed solvent as used in Example 3, and left to stand at room temperature for 12 hours. Crystals of a complex obtained by filtering the solution were recrystallized once from the same mixed solvent as above, filtered, and dried to give 1.15 g of prismatic crystals. These crystals were a complex in which the mole ratio of (−)-A to cis-(−)-F was 1:1. The complex had a melting point of 125° to 127° C. and a $[\alpha]_D$ of −122°.

When these crystals were heated in the same way as in Example 3, 0.28 g of cis-(−)-F ($[\alpha]_D = -98.1°$) was obtained.

When the filtrate from which the complex was separated was left to stand at room temperature for 6 hours, a complex in which the mole ratio of (−)-A to trans-(+)-F was 1:1 precipitated.

The complex was recrystallized twice from the mixed solvent, filtered, and dried to give 1.59 g of colorless needle-like crystals. The crystals had a melting point of 132° to 134° C. and a $[\alpha]_D$ of −99.3°.

When the crystals were heat-treated, 0.39 g of trans-(+)-F ($[\alpha]_D = +79.4°$) was obtained.

EXAMPLE 7

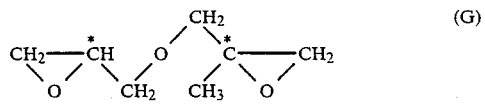

The same (−)-A as in Example 3 (4.83 g) and 2.88 g of a diastereomeric mixture of 2,3-epoxypropyl-2′,3′-epoxy-2′-methylpropyl ether were dissolved in 20 ml of the same mixed solvent as in Example 3, and left to stand at room temperature for 12 hours. Crystals of a complex obtained by filtration were recrystallized three times from the mixed solvent, filtered, and dried to give 1.39 g of colorless prismatic crystals. The crystals were a complex in which the mole ratio of (—)-A to (—)-G was 1:1. The complex had a melting point of 98° to 100° C. and a $[\alpha]_D$ of $-97.7°$.

When the crystals were heated as in Example 3, 0.31 g of (—)-G ($[\alpha]_D = -20.2°$) was obtained.

EXAMPLE 8

Optically pure levorotatory 1,6-di-o-chlorophenyl-1,6-diphenylhexa-2,4-diyne-1,6-diol ($[\alpha]_D = -122°$; mp. 127°–129° C.; 4.83 g=0.01 mole) and 3.42 g (0.02 mole) of racemic 1-acetoxy-2,3-dichloropropane were dissolved in a mixed solvent composed of 10 ml of ether and 10 ml of petroleum ether, and left to stand at room temperature for 12 hours. The resulting crystals were collected by filtration, and recrystallized once from the same mixed solvent as above to give 3.31 g of colorless prismatic crystals which were a complex having a melting point of 93° to 95° C. and a $[\alpha]_D$ of $-86.8°$ and in which the mole ratio of the above compounds was 1:1. The crystals were heated to about 150° C. under reduced pressure (25 mmHg) to give 0.87 g of dextrorotatory 1-acetoxy-2,3-dichloropropane having a $[\alpha]_D$ of $+18.6°$.

Separately, the solvent of the mother liquor left after separation of the crystals by filtration was evaporated, and the residue was distilled under reduced pressure to give 2.10 g of levorotatory 1-acetoxy-2,3-dichloropropane having a $[\alpha]_D$ of $-2.89°$.

The resulting levorotatory 1-acetoxy=2,3-dichloropropane (2.10 g) and 5.93 g of dextrorotatory 1,6-di-o-chlorophenyl-1,6-diphenylhexa-2,4-diyne-1,6-diol $[\alpha]_D = +122°$) were dissolved in 20 ml of a mixed solvent of ether and petroleum ether, and left to stand at room temperature for 12 hours to precipitate a complex. The complex was recrystallized once from the same mixed solvent as above and distilled under reduced pressure to give 0.64 g of levorotatory 1-acetoxy-2,3-dichloropropane $[\alpha]_D = -18.6°$.

What is claimed is:

1. A method of optically resolving a racemate or a diastereomeric mixture of a compound selected from the group consisting of glycidyl ester compounds represented by the formula:

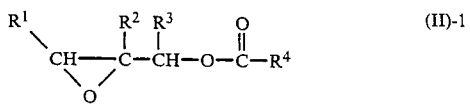

wherein $R^1$, $R^2$ and $R^3$, independently from each other, represent H or $CH_3$, $R^4$ represents a $C_1$–$C_6$ alkyl, $C_6$–$C_{10}$ aryl, $C_6$–$C_{10}$ aryl-$C_1$–$C_2$-alkyl, $C_6$–$C_{10}$ aryl-$C_2$–$C_4$-alkenyl or $C_2$–$C_4$ alkenyl group, and when $R^4$ represents an alkyl group, $R^1$ and $R^3$ together may represent the moiety

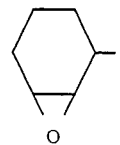

together with the group

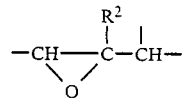

in the formula,
glycidyl ether compounds represented by the formula:

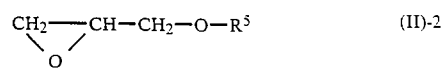

wherein $R^5$ represents a $C_1$–$C_6$ alkyl, $C_6$–$C_{10}$ aryl, $C_2$–$C_4$ alkenyl or

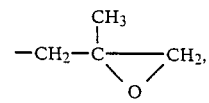

and compounds represented by the formula:

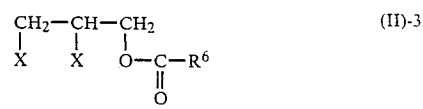

wherein X represents a halogen atom, and $R^6$ represents a $C_1$–$C_6$ alkyl, $C_6$–$C_{10}$ aryl, $C_6$–$C_{10}$ aryl-$C_1$–$C_2$-alkyl, $C_6$–$C_{10}$ aryl-$C_2$–$C_4$-alkenyl or $C_2$–$C_4$ alkenyl group which comprises contacting said racemate or diastereomeric mixture with an optically active form of a compound having the following formula (I):

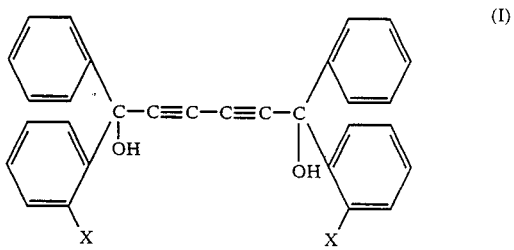

wherein X represents a halogen atom,
to form an inclusion complex compound having the optically active compound of formula (I) as a host, and separating the resulting complex compound from the mixture.

2. The method of claim 1 which comprises contacting said racemate or diastereomeric mixture with the optically active form of the compound of formula (I) in a solvent, and recovering the optically active compound from the inclusion complex compound.

3. The method of claim 2 wherein the resulting solid complex compound is separated from the liquid phase by filtration and the recovered complex compound is purified by recrystallization.

4. The method of claim 2 wherein the optically active guest compound is recovered from the inclusion complex compound by distillation under heat.

5. The method of claim 2 wherein the optically active guest compound is recovered from the inclusion complex compound by substitution by a polar solvent.

6. The method of claim 2 wherein the optically active guest compound is recovered from the inclusion complex compound by chromatography.

7. The method of claim 2 which further comprises recovering the enantiomorph of the racemate mixture which does not form the inclusion complex compound from the liquid phase remaining after separation of the inclusion complex compound from the liquid phase.

8. The method of claim 1 which comprises contacting said racemate or diastereomeric mixture with the optically active form of the compound of formula (I) in proportions such that the guest compound of the inclusion complex compound is present in about 0.25 to about 4 moles per mole of the host compound.

9. The method of claim 1 for optically resolving a racemate or diastereomeric mixture of said unsubstituted glycidyl ester compounds represented by the formula (II)-1.

10. The method of claim 9 wherein $R^4$ represents a $C_1$–$C_4$ alkyl group.

11. The method of claim 1 for optically resolving a racemate or a diastereomeric mixture of a glycidyl ether compound represented by the formula (II)-2.

12. The method of claim 11 wherein $R^5$ represents a $C_1$–$C_4$ alkyl group or a phenyl group.

13. The method of claim 1 for optically resolving a racemate or a diastereomeric mixture of beta-dihalohydrin ester compounds represented by the formula (II)-3.

14. The method of claim 13 wherein $R^6$ is a $C_1$–$C^4$ alkyl group.

15. The method of claim 1 for optically resolving a racemate or a diastereomeric mixture of a glycidyl ester compound of formula (II)-1 selected from the group consisting of: glycidyl acetate, 2-methylglycidyl acetate, glycidyl propionate, glycidyl butyrate, glycidyl benzoate, glycidyl cinnamate, glycidyl alpha-naphthoate, glycidyl beta-naphthoate, glycidyl alpha-naphthylacetate, glycidyl beta-naphthylacetate, glycidyl alpha-naphthoxyacetate, glycidyl beta-naphthoxyacetate, glycidyl acrylate, glycidyl methacrylate, 1-methyl-2,3-epoxy-propyl acetate, 2,3-epoxybutyl acetate, 1-methyl-2,3-epoxy-butyl acetate, and 2,3-epoxy-cyclohexyl acetate.

16. The method of claim 1 for optically resolving a racemate or a diastereomeric mixture of a glycidyl ether compound of formula (II)-2 selected from the group consisting of: methyl glycidyl ether, allyl glycidyl ether, n-butyl glycidyl ether, iso-butyl glycidyl ether, phenyl glycidyl ether, alpha-naphthyl glycidyl ether, beta-naphthyl glycidyl ether, 2,3-epoxypropyl-2',3'-epoxy-2'-methylpropyl ether, and diglycidyl ether.

17. The method of claim 1 for optically resolving a racemate or a diastereomeric mixture of a beta-dihalohydrin ester compound of formula (II)-3 selected from the group consisting of: 1-acetoxy-2,3-dichloropropane, 1-butanoxy-2,3-dichloropropane, and 1-acetoxy-2,3-dibromopropane.

18. The method of claim 1 wherein X in formula (I) is chlorine, bromine, iodine, or fluorine.

* * * * *

UNITED STATES PATENT AND TRADEMARK OFFICE
CERTIFICATE OF CORRECTION

PATENT NO. : 4,841,081
DATED : June 20, 1989
INVENTOR(S) : FUMIO TODA ET AL.

It is certified that error appears in the above-identified patent and that said Letters Patent is hereby corrected as shown below:

Claim 9, lines 2-3, delete "unsubstituted".

Claim 14, line 1, "$C_1-C^4$" should be deleted and --$C_1-C_4$-- inserted.

Signed and Sealed this

Twenty-second Day of May, 1990

Attest:

HARRY F. MANBECK, JR.

*Attesting Officer*      *Commissioner of Patents and Trademarks*